| United States Patent [19] | [11] Patent Number: 4,764,475 |
| Brown | [45] Date of Patent: Aug. 16, 1988 |

[54] PANCREAS DEPENDANT IMMUNOASSAY FOR DETERMINING SUBPOPULATIONS OF MONOCLONAL ANTIBODIES TO SOMATOSTATIN.

[75] Inventor: John C. Brown, Vancouver, Canada

[73] Assignee: The University of British Columbia, Vancouver, Canada

[21] Appl. No.: 936,460

[22] Filed: Dec. 1, 1986

[51] Int. Cl.[4] ............... G01N 33/567; G01N 33/577; A61K 37/04
[52] U.S. Cl. ...................................... 436/548; 435/7; 424/85; 436/817
[58] Field of Search ......................... 435/548; 424/85; 436/817

[56] References Cited

U.S. PATENT DOCUMENTS 3,995,019  11/1976  Jerome ............................. 436/817
4,185,084  1/1980   Mochida et al. .................... 436/817
4,599,229  7/1986   Maccecchini ...................... 424/85

OTHER PUBLICATIONS

McIntosh et al., Chem. Abstracts 94:202973w (for Can. J. Phys. Pharmacol., 59(5), 468, (1981)).
McIntosh et al., Chem. Abstracts, 90:68566c (for Z. Gastroenterol., 16(5), 330, (1970)).
McIntosh et al., Chem. Abstracts, 89:127026f (for Gut Hormone, (1978), 453-6, Bloom (ed)).

*Primary Examiner*—Howard E. Schain
*Assistant Examiner*—J. Kushan
*Attorney, Agent, or Firm*—Ciotti & Murashige, Irell & Manella

[57] ABSTRACT

A correlation has been demonstrated between the ability of an antibody to block the inhibitory action of somatostatin on the gastric inhibitory peptide(GIP)-stimulated release of insulin from the pancreas in vitro and the ability to stimulate growth in vivo. Antibodies which are identified in the GIP-stimulated insulin release assay are also capable of elevating the levels of growth hormone in vivo.

6 Claims, 2 Drawing Sheets

PANCREAS DEPENDANT IMMUNOASSAY FOR DETERMINING SUBPOPULATIONS OF MONOCLONAL ANTIBODIES TO SOMATOSTATIN.

FIELD OF THE INVENTION

The invention relates to animal husbandry, in particular to methods for stimulating the growth or productivity of domesticated animals. Specifically, the invention relates to the uses of selected monoclonal antibody preparations for growth regulation of these animals.

BACKGROUND ART

The regulation of growth in vertebrates is believed to involve the interaction of the mechanisms for the release of growth hormone with the 14-amino acid peptide somatostatin or its various alternative forms. At least one function of somatostatin in vivo is to depress growth, presumably by interaction with this system.

Accordingly, it has been suggested that antibodies reactive with somatostatin should be capable of stimulating growth by depressing the action of somatostatin with the growth regulatory system, and it has been shown that rats administered antisomatostatin antiserum show increases in growth hormone levels; in particular the decrease in growth hormone levels ordinarily observed in response to stress is mitigated (Chihara, K., et al, *Endocrin* (1978) 103:1916; Arimura, et al, *Endocrin* (1976) 98:540).

Accordingly, attempts have been made to depress somatostatin activity using the immune system. Spencer, et al (*Animal Production* (1981) 31:376; *Veterinary Record* (May 22, 1984), p. 484) have shown that lambs injected with somatostatin linked to carrier protein raised antibodies against the conjugate and showed enhanced weight gain. Varner et al, *Endocrinology* (1980) 106:1027, reported that growth hormone concentrations in serum were higher in lambs autoimmunized against somatostatin than in controls; however, growth was not enhanced in these animals. Additional reports of attempts to use this system to enhance growth or demonstrate increases in levels of growth hormone include Lovinger, R., et al, *Endocrinol* (1974) 95:743; Kato, Y., *Endocrinol* (1974) 95:1608.

The interaction of somatostatin with the growth hormone system has also been demonstrated by regulating somatostatin levels directly. Cowan, J. S., *Canadian J Physiol Pharmacol* (1984) 62:199-207, showed withdrawal of somatostatin initiated bursts of growth hormone secretion in dogs. It has also been shown that growth hormone releasing factor (GRF) will result in elevated growth hormone concentration only at low somatostatin levels (Cowan, J. S., et al, *Canadian J Physiol Pharmacol* (1985) 63:AIX (Abstract)).

The production of monoclonal antibodies which are immunoreactive with somatostatin has been reported. Buchan, A. M. J., et al, *Histochemistry* (1985) 83:175-180, describe the production of antibodies initially screened for immunoreactivity with somatostatin. To produce these antibodies, somatostatin-14 (cyclic) was conjugated to keyhole limpet hemocyanin (KLH) (Cal Biochem) using carbodiimide and dialyzed overnight at 4° C. The dialyzed preparation was used to immunize BIO.BRSgSn mice (Jackson Laboratories, Bar Harbor, Me.) which were injected three times with 30 nM of the conjugate, and the sera were titrated for antisomatostatin using an ELISA assay. The spleen from the mouse showing the best antibody response was fused with NSI cells according to the method of Kohler and Milstein, *Eur J Immunol* (1976) 6:511-521, as modified by Fazekas de St. Groth, et al, *J Immunol Meth* (1980) 35:1-21, and of Oi, V. T., et al, *Selected Methods in Cellular Immunology* (1980), Michel, B. B., et al, eds. W. H. Freeman, San Francisco.

Clones were screened using the ELISA method of Boller, A., et al, *Bull WHO* (1976) 53:55-65. Positively testing clones were grown and the supernatants retested for specificity in ELISA against somatostatin, KLH, and an unrelated antigen, ferredoxin.

Four hybrids which showed the correct specificity for somatostatin were cloned out by limiting dilution 5 times and grown as ascites tumors of irradiated outbred mice. The antibodies could be partially purified from the fluid by precipitation by 50% ammonium sulfate, and then dialyzed and lyophilized.

These four antibodies were shown to be immunocytochemically reactive with a number of cells associated with the neural and digestive system. A description of the histochemical activity of these antibodies is set forth in the above-referenced article by Buchan et al and in the report by Vincent, S. R., et al, *J Compar Neurol* (1985) 238:169-186.

A U.S. Pat. No. 4,599,229, claims methods to promote growth using both polyclonal antisera against somatostatin and monoclonal antibodies prepared from hybridomas formed by fusions involving lymphocytes from immunized animals. The disclosure proposes screening hybridoma supernatants against somatostatin per se, however, and fails to disclose that only a fraction of antibodies thus screened will in fact be effective in enhancing growth.

DISCLOSURE OF THE INVENTION

It has now been found, unexpectedly, that only those antibodies immunoreactive with somatostatin that specifically inhibit somatostatin's effect on insulin release are effective in controlling its effect on the growth system. Accordingly, a method is provided whereby monoclonal antibody preparations may be screened for the identification of those antibodies which are effective in a growth-enhancing preparation. This, unlike the art cited, permits the effective use of monoclonal antibodies to regulate growth in animals.

Accordingly, in one aspect, the invention relates to a method to identify monoclonal antibodies effective in enhancing growth, which method comprises assaying the ability of the monoclonal antibody preparation to effect insulin release by pancreas tissue in vitro. Somatostatin inhibits gastric inhibitory polypeptide (GIP)-stimulated release of insulin from pancreas preparations. Monoclonal antibody preparations which are capable of restoring the insulin release in the presence of somatostatin test positive in this assay. These same antibodies are also capable of enhancing growth of animals when administered using standard procedures. Antibodies which fail to restore insulin release from the pancreas are incapable of stimulating growth. Thus, the method of the invention comprises screening antibody preparations using GIP-stimulated insulin release from pancreas as an assay.

In another aspect, the invention relates to a method to enhance growth in animals by administering to them an effective amount of the antibodies which have been so identified.

MODES OF CARRYING OUT THE INVENTION

General Aspects

Figure 1:
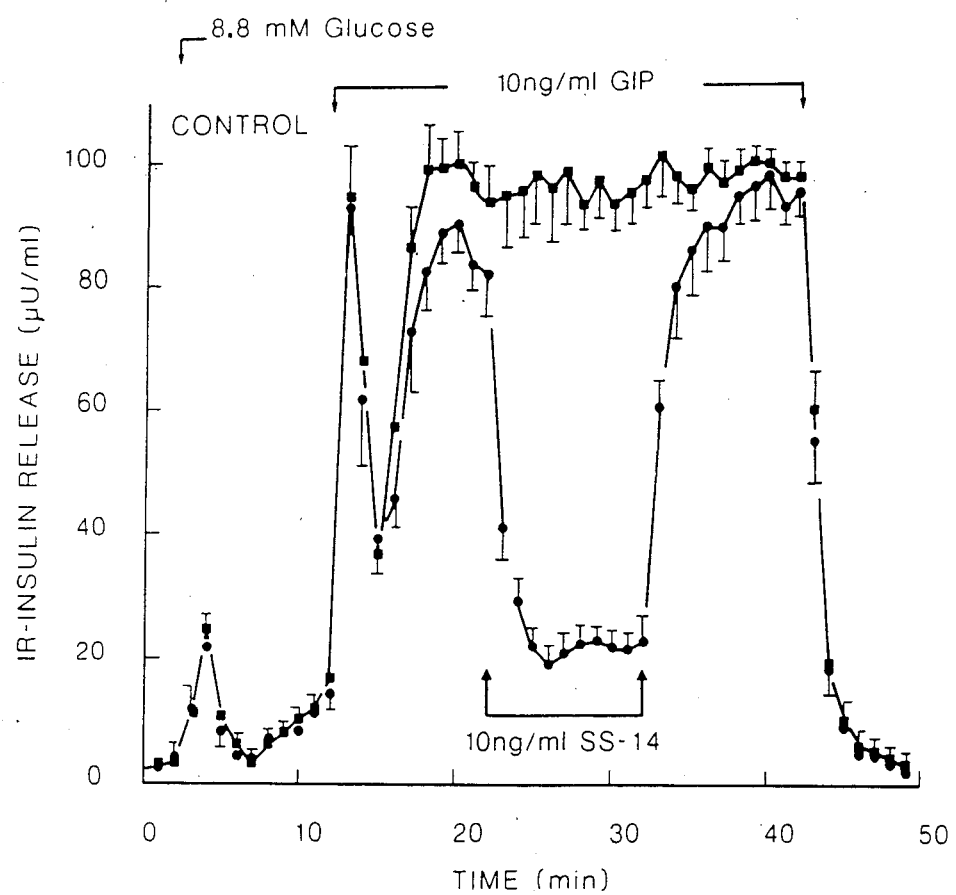
FIG. 1 shows insulin release stimulated by GIP, and inhibited by somatostatin in the absence of added antibodies.

As used herein, "immunologically reactive with" refers to the ability of an immunoglobulin or a fragment thereof to react specifically with an antigen. In the context of the present invention, species which are "immunologically reactive with" somatostatin complex with somatostatin to the exclusion of other proteins. The immunologically reactive species may be whole immunoglobulins of any class, including IgG, IgM, and so forth, or also fragments of individual immunoglobulins having the variable region present. Preparation methods for such fragments are well understood in the art, and the most commonly used fragments are the Fab fragment, obtained by papain digestion, the F(ab')$_2$ fragments obtained by pepsin digestion, and the Fab' fragments obtained by reduction of these. The use of fragments rather than whole immunoglobulins has some advantages in cross-species administration, since the fragments tend to be less immunogenic in nonhomologous species than the whole antibody.

The screening test disclosed herein involves the interaction of somatostatin with GIP in regulating insulin release. A particular assay is described which quantitates this effect and interaction. However, other analogous protocols may be used at the convenience of the practitioner. Rather than perfused pancreas, for example, isolated and cultured Islets of Langerhans cells may be used as subjects. In addition, since it is clear from the discovery disclosed herein that the same pharmacophore is utilized in the insulin release reaction and in regulation of the growth system, a "second tier" assay can be used as a criterion for selecting the appropriate monoclonal preparation in which proposed antibody preparations are tested for cross-reactivity with antibodies known to be positive in the insulin-release screen. Antibodies cross-reacting with the antibodies testing positive will enhance growth.

"Cross-reactive" antibodies are those which react with the same epitope. Cross reactivity is generally determined using competition assays in which, for example, the ability of labeled antibody A to bind to antigen is diminished by the presence of increasing levels of antibody B with which it is cross reactive; or, for example, the amount of labeled antigen bound to a solid support containing antibody A is diminished by the presence of antibody B.

In general, the monoclonal antibodies screened by the assay method suggested below are useful in enhancing the growth of a vertebrate subject, presumably by counteracting the effect of somatostatin on the systems responsible for the release of growth hormone.

The results of administration of the antibodies of the invention are not limited, however, to stimulation of growth; indeed, growth hormone is known to affect metabolism and development in additional ways. Thus, for example, in the bovine system, the method of the invention may be used to stimulate milk production, in fish, the method may be used to stimulate immune system development.

The method of the invention is successful in vertebrates in general, including mammals, in particular, domesticated animals, birds, reptiles (if desired), and fish. As set forth below, of course, the manner of administration and dosage depends on the nature of the vertebrate subject and the result desired.

Most of the previous work has been done with mammalian subjects. However, avian subjects are similarly benefited by the use of the monoclonal antibodies of the invention, and it is clear that the applications to avian subjects are of great economic importance. For example, chickens are raised under factory-type conditions and hundreds of thousands are sent to markets each day in North America. Shortening of growth time would clearly increase profitability.

In addition, the monoclonal antibodies of the invention are useful in increasing the growth rate of both Pacific and Atlantic salmon species in order to enhance the economics of the fish hatchery industry. The increased growth rate not only reduces the time necessary for maintenance in fresh water, where the costs of maintenance are higher than in sea water, but also shortens the time for attainment of immunocompetence. Immunocompetence is weight dependent; it begins when the salmon weigh approximately 1.0 g and is complete by the time they weight about 3.0 g. Of course, the treatment can also increase the harvest size of the fish. In addition, if given to smolts just prior to transferring to salt water, the increased growth hormone secreted performs a mediating function in aiding the fresh water-salt water transition.

THE ASSAY METHOD

The preferred assay method for the initial screen takes advantage of the known interaction between GIP and somatostatin on insulin release (McIntosh, C.H.S., et al, *Gut Peptides* (1979), Miyoshi, A., ed, Kodansha and Elsevier, Tokyo/Amsterdam, p. 100; McIntosh, C.H.S. et al, *Canadian J Physiol Pharmacol* (1981) 59:468). Specifically, it has been shown that somatostatin inhibits GIP-stimulated insulin release in the dog (Pederson, R. A., et al, *Canadian J Physiol Pharmacol* (1975) 53:1200). The hypothesis has been that since GIP has also been shown to stimulate somatostatin release (Ipp, E., et al, *J Clin Invest* (1977) 60:1216), the system is self-regulating by virtue of bursts of GIP simultaneously stimulating the release of insulin and its own inhibitor, somatostatin.

In the assay, rat pancreas tissue is isolated and perfused according to the method of Grodsky, G. M., et al, *Metabolism* (1967) 16:222: The pancreas tissue from overnight-fasted, anesthetized rats is removed and perfused with a modified Krebs/Ringer bicarbonate buffer containing 3% dextran, clinical grade, and 0.2% bovine albumin, RIA grade. The perfusate is warmed to 37° C. and gassed with 95% oxygen:5% $CO_2$ to pH 7.4. Effluent from the cannulated portal vein is collected at 1 min intervals at a flow rate of 4 ml/min. Prior to experimental time zero, the pancreas is perfused for a 10 min period with buffer containing $4.4 \times 10^{-3}$ M glucose. Experiments are performed during perfusion with $8.8 \times 10^{-3}$ M glucose, and after establishing a steady state insulin secretion.

For the assay, porcine GIP is infused via a sidearm attachment at a concentration calculated to achieve a perfusate level of $2 \times 10^{-9}$ M for a 30 min period.

Somatostatin is infused to achieve a final concentration of $6.25 \times 10^{-9}$ M. The monoclonal antibodies to be tested are administered to achieve a final concentration of 1 μg/ml. (Based on the ELISA determination that 10 ng somatostatin can be neutralized by 300 ng Mab.)

The antibody is administered at time zero in excess prior to the introduction of porcine GIP and somatostatin.

The administration of glucose alone stimulates the secretion of some insulin. The infusion of 2 nM GIP is started at 12 min and continued for 30 min to produce a prompt increase in insulin release which is biphasic in nature. There is a plateau of stimulation preceded by a spike response, as shown by the squares in FIG. 1. However, this response is dramatically altered when somatostatin is introduced, as shown by the circles in FIG. 1. Cyclic somatostatin 14 is introduced into the perfusing buffer for a 10 min period at time 22 min. The infusion of somatostatin introduces an immediate inhibition of GIP-stimulated insulin release followed by a rapid increase to presomatostatin levels at continued perfusion.

Figure 2:
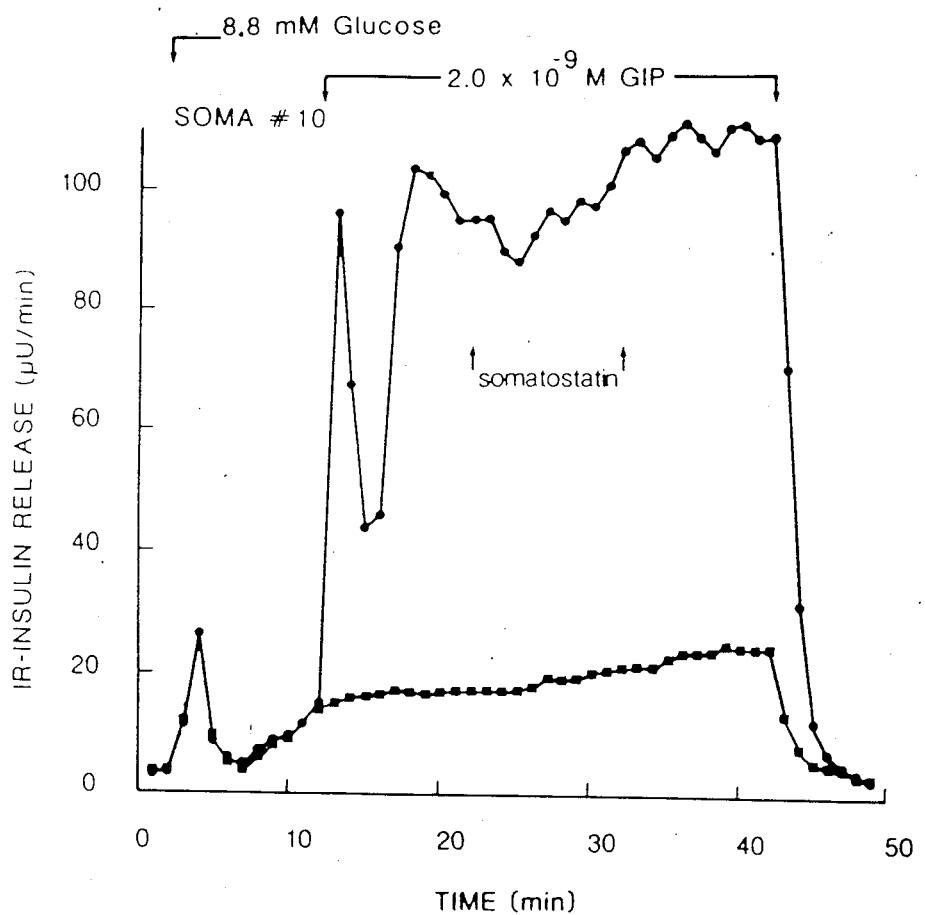
FIG. 2 shows the effect on the insulin release pattern of FIG. 1 when antisomatostatin antibodies of various effectiveness are added.

A negative result in this test results in the pattern shown in FIG. 1 by the solid circles (somatostatin introduced as shown) being unaltered. However, when monoclonal antibody preparations which react with the pharmacophore important in this inhibition are used, the effect of somatostatin is blocked, as shown in FIG. 2 (solid circles). The resulting pattern resembles that of the solid squares in FIG. 1; the high insulin level is maintained even when somatostatin is introduced.

The four monoclonal antibody preparations described by Buchan, A.M.J., et al, supra, were tested in this assay, and only one, designated SOMA-10, produced complete blockage. Partial blockade was observed with SOMA-08. On the other hand, two antisomatostatin monoclonal preparations, SOMA-03 and SOMA-20 were inactive in this assay. This finding is particularly surprising in view of the suggestion in the literature that the "essential pharmacophore" of somatostatin is the mid-region sequence Phe-Trp-Lys-Thr-Phe-Trp-Lys-Thr (Veber, D. F., et al, Nature (1979) 280:512). SOMA-20, inactive in the insulin-release assay was reactive with this peptide; SOMA-10, which was active in the assay, was not.

PREPARATION OF THE MONOCLONAL ANTIBODY

Antibody preparations which are reactive with somatostatin and useful in the invention can be prepared in a variety of ways in addition to that disclosed by Buchan et al. Alternate immortalization techniques and tumor cells which normally secrete antibodies can also be used as sources. The method of preparation of antibody secreting cells may include the Kohler/Milstein procedure using fusion partners from immunized animals in a more-or-less standard approach, or these potential fusion partners may be immortalized by other means such as introduction of viral genes. In addition, cells may be found which secrete antisomatostatin antibodies natively, and these cells may either themselves be immortal, if they are tumorous, or may be immortalized by transforming them.

Any cell lines secreting antisomatostatin antibodies may be used in the method of the invention to screen for those immunoglobulins which are effective in growth enhancement.

Screening Tests

The monoclonal antibody preparations may be screened by ability to effect insulin secretion, as suggested above and exemplified by the perfused rat pancreas assay. An alternative screen, and perhaps more easily performed however, comprises cross-reactivity of the test antibody with an antibody which has already passed the pancreas perfusion screen. For such tests, standard competitive ELISA, RIA, or other competitive immunoassay techniques may be used. In these procedures, depending on the protocol, the ability of the test antibody to cross react with standard antibody for somatostatin active in the insulin release assay may be assessed. This may be done, for example, by showing competition with labeled antibody or the ability of the test antibody to prevent the binding of labeled somatostatin to immobilized standard antibody may be used. A large variety of protocols for such competitive assays are known in the art, and will be evident to practitioners thereof.

Administration to Enhance Growth

The monoclonal antibody preparations of the invention are administered to various vertebrates in a manner appropriate to the nature of the active ingredient being administered, the nature of the subject vertebrate, and the individual variation of the desired growth patterns. In general, it is more straightforward to utilize monoclonal antibodies derived from the same species to which treatment is administered. Using monoclonal antibodies of homologous origin minimizes problems of immunogenicity and side reactions. If homologous monoclonals are used, it is unlikely that special precautions need be taken to mitigate these problems.

However, monoclonal antibodies of the invention can be derived from species different from that to which they are administered. A number of methods are available whereby the cross-species immunosensitivity can be overcome. In one approach, the antibody can be conjugated to polyethylene glycol to diminish its immunogenicity. Such conjugation procedures are disclosed, for example, in U.S. Pat. No. 4,261,973 and GB No. 1,578,348. In other approach, only the Fab or Fab' fragments are used. In still another approach, the monoclonals are administered to the animal at an early age prior to the maturity of their own immune systems.

The administration of the monoclonal antibodies of the invention to mammalian subjects is achieved in a manner suitable for the administration of protein substances, by direct injection, by intravenous administration, or by application through a slow-release composition. The amount of antibody to be administered varies, of course, according to the mode of administration, the degree of growth or development enhancement desired, and the metabolism of the animal. In general, however, the amount of antibody to be administered is in the range of 10–500 μg/kg of subject animal.

For avian and fish subjects, of course, the method of administration differs from that suitable for mammalian subjects, although the does range on a per kilogram basis is roughly the same. The most practical way for administration to poultry is by formulating the antibody preparation into the feed. As the antibodies or glycoproteins, formulation must be such as to diminish the degradation of the protein in the digestive system and to assure transfer of the preparation's active ingredient into the bloodstream. For administration to fish, it is generally adequate to include the antibodies in the aqueous medium in which the fish are enclosed, since the subjects are capable of uptake of the active ingredient directly through the gill structure. While there is little problem with degradation or lack of uptake for these subjects, the fish must be temporarily confined to a small enough volume that dilution does not prevent adequate levels being infused.

Administration protocols are also variable, and the above dosage ranges may be administered in a slow release form over a period of several days, or by means of a series of injections of fractions of the total dose.

Compositions for administration of the invention are those conventional in the art for administration of proteins, and include liquid excipients such as saline or dextrose-containing saline solution, lyophilized compositions which can be dispersed in liquid to result in injectable compositions, and the like. Additional ingredients designed to enhance stability, maintain pH, or create an emulsion may also be used. Suitable formulation may, for example, be found in *Remington's Pharmaceutical Sciences,* Mack Publishing Co., Easton, PA, latest edition.

Proteins may also be administered transdermally by means of substances which enhance transfer of materials across mucosal membranes. A number of such transdermal compositions are disclosed in the art, and include, for example, steroid derivatives and various detergent compositions.

EXAMPLES

The following example is intended to illustrate but not to limit the invention.

EXAMPLE 1

Regulation of Growth Hormone Release in Dogs Using Monoclonal Antibodies

Five dogs were used in the determinations illustrated here. The dogs were administered pairs of IV injections wherein each pair comprises first 0.5 µg/kg then 2 µg/kg of hpGRF (1-44). The first pair is administered during a control period followed by the next two pairs during a period of somatostatin infusion, the next pair during another control period, and the last pair following the intravenous injection of 12-24 µg/- kg of the monoclonal antibody. Thus, each animal had a total of 10 injections, 4 during somatostatin infusions, 4 during control periods, and 2 following the antibody administration. The various injections took place at 40 min intervals. The infusion of somatostatin was 0.15 µg/kg/min, a rate shown to be the minimum to block spontaneous GH secretory bursts.

The animals were followed by assaying blood samples for GH every 5 min, or shorter periods if needed, in triplicate using radioimmunoassay. Determination of plasma glucocorticoids confirmed that the animals were not stressed. While GRF enhanced the serum levels of GH in the control periods, the increase in secretion lasting 15-38 min, when GRF was injected during somatostatin infusion, these bursts of GH secretion did not take place.

In three dogs, ceasing somatostatin infusion permitted the animals to return to the pattern of GH secretion when GRF was administered.

In four of the five dogs, administration of SOMA-10 evoked immediate large bursts of GH release lasting 20-28 min, and a second GRF injection evoked a GH response similar to the control period. Basal GH was generally elevated.

Apparently, therefore, somatostatin is able to offset the effect of GRF, but this effect is, in turn, removed by the appropriate antibody. In control experiments using SOMA-20 and SOMA-03, which were inactive in the insulin-release assay, no GH secretion spike was observed. SOMA-8, which showed partial activity in the insulin-release assay, gave intermediate results.

I claim:

1. A method to identify a monoclonal antibody preparation which is effective in stimulating growth hormone release in a vertebrate, which method comprises assaying a candidate monoclonal antibody preparation that is immunoreactive with somatostatin by testing its ability to restore gastric inhibitory peptide (GIP)-stimulated insulin release from the pancreas in the presence of otherwise inhibiting amounts of somatostatin.

2. The method of claim 1 wherein the identification is conducted in isolated perfused pancreas.

3. The method of claim 2 wherein the isolated pancreas is rat pancreas.

4. A method to identify a monoclonal antibody preparation which is effective in stimulating growth hormone release in a vertebrate, which method comprises assaying a candidate monoclonal antibody preparation (the test preparation) that is immunoreactive with somatostatin by testing its ability to immunologically cross-react with a preparation shown to be able to restore GIP-stimulated insulin release from the pancreas in the presence of otherwise inhibitory amounts of somatostatin (the standard preparation).

5. The method of claim 4 which comprises measuring the inhibition by a test preparation of the binding of somatostatin to labeled standard preparation.

6. The method of claim 4 which comprises measuring the inhibition by a test preparation of the binding of labeled somatostatin to immobilized standard preparation.

* * * * *